United States Patent [19]

Balasubramanyan et al.

[11] 4,073,925
[45] Feb. 14, 1978

[54] FUNGICIDALLY EFFECTIVE IMIDAZOLES AND USE THEREOF AGAINST FUNGAL PESTS

[75] Inventors: Sugavanam Balasubramanyan, Wokingham; Margaret Claire Shephard, Maidenhead, both of England

[73] Assignee: Imperial Chemical Industries Limited, London, England

[21] Appl. No.: 718,205

[22] Filed: Aug. 26, 1976

[30] Foreign Application Priority Data

Dec. 12, 1975 United Kingdom ............... 51039/75
Jan. 8, 1976 United Kingdom .................. 671/76

[51] Int. Cl.² .................... C07D 233/60; A01N 9/22
[52] U.S. Cl. .............................. 424/273 R; 548/336; 548/341
[58] Field of Search ................. 260/309; 424/273; 548/336, 341

[56] References Cited

U.S. PATENT DOCUMENTS 3,755,349  8/1973  Timmler et al. ..................... 260/309
3,867,453  2/1975  Mukaiyama et al. ......... 260/570 AB

OTHER PUBLICATIONS

Brust et al., Chem. Abst. 1966, vol. 65, column 5446.
Kraemer et al., Chem. Abst. 1974, No. 133441t.
Mukaiyama et al., Chem. Abst. 1975, vol. 82, No. 3990b.
Tsizin et al., Chem. Abst. 1975, vol. 83, No. 73399k.

*Primary Examiner*—Natalie Trousof
*Attorney, Agent, or Firm*—Cushman, Darby & Cushman

[57] ABSTRACT

A compound the formula:

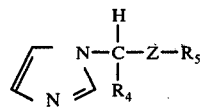

wherein $R_4$ is alkenyl or alkynyl of up to 8 carbon atoms or aralkyl of up to 8 carbon atoms, the aralkyl being optionally substituted with 2 halogen, alkyl of up to 8 carbons, nitro, trifluoromethyl, cyano, methoxy or methylenedioxy, $R_5$ is cycloalkyl or branched chain alkyl of up to 8 carbon atoms, and Z is C = O, or a fungicidal salt of such compound.

8 Claims, No Drawings tween inoculation and assessment varied from 3 to 10 days according to the disease and environment.

The disease control was recorded by the following grading:
4 = No disease
3 = 0-5%
2 = 6-25%
1 = 26-60%
0 = >60%

The results are shown in Table II.

TABLE I

| COMPOUND NO. | DISEASE (DAYS BETWEEN INFECTION AND ASSESSMENT) | | | | | |
|---|---|---|---|---|---|---|
| | Puccinia recondita in wheat (10 days) | Phytophthora infestans in tomato (3 days) | Plasmopara viticola in vines (7 days) | Piricularia oryzae in rice (7 days) | Botrytis cinerea in tomatoes (3 days) | Erysiphe graminis in barley (7 days) |
| 1 | 3 | 3 | — | 1 | 3 | 4 |
| 2 | 3 | — | 0 | 0 | 0 | 4 |
| 3 | — | 0 | 0 | 3 | 4 | 4 |
| 4 | — | 0 | 0 | 1 | 4 | 4 |
| 5 | 0 | 0 | 0 | 3 | 3 | 4 |
| 6 | 3 | 1 | 0 | 1 | 4 | 4 |
| 7 | | | | | | |
| 8 | | | | | | |
| 9 | | | | | | |

We claim:
1. A compound of the formula:

$$\begin{array}{c} H \\ | \\ N-C-Z-R_5 \\ | \\ R_4 \end{array}$$

wherein $R_4$ is alkenyl or alkynyl each of up to 8 carbon atoms or aralkyl of up to 8 carbon atoms, said aralkyl being optionally substituted with halogen, alkyl of up to 8 carbon atoms, nitro, trifluoromethyl, cyano, methoxy or methylenedioxy, $R_5$ is cycloalkyl or branched chain alkyl of up to 8 carbon atoms, and Z is C = O, or a fungicidal salt of such compound.

2. A compound as claimed in claim 1 wherein $R_4$ is benzyl or α-methylbenzyl optionally ringsubstituted with halogen, cyano or trifluoromethyl and $R_5$ is t-butyl.

3. A compound according to claim 1 selected from the group consisting of compounds where $R_5$ is t-butyl and $R_4$ has one of the following values:

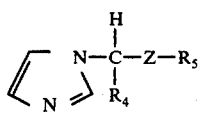

CH$_2$Ph

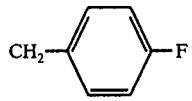

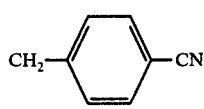

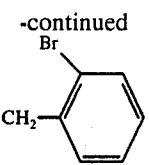

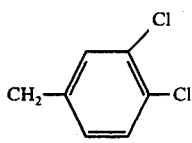

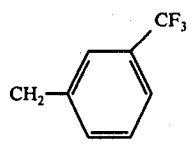

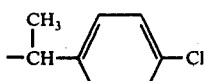

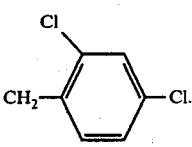

4. A compound according to claim 3 wherein $R_4$ is

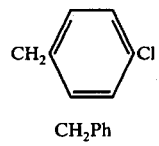

and $R_5$ is t-Bu.

5. A fungicidal composition consisting essentially of as active ingredient, a fungicidally effective amount of a compound or salt as claimed in claim 1, and a carrier for the active ingredient.

6. A fungicidal composition consisting essentially of, as active ingredient, a fungicidally effective amount of a compound or salt as claimed in claim 2 and a carrier for the active ingredient.

7. A method of combating fungal diseases in a plant, said method consisting essentially of the step of applying to the plant, or to the locus of the plant, a fungicidally effective amount of a compound or salt as claimed in claim 1.

8. A method of combating fungal diseases in a plant, said method consisting essentially of the step of applying to the plant, or to the locus of the plant, a fungicidally effective amount of a compound or salt as claimed in claim 2.

* * * * * and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersions or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, as well as stabilising agent(s), for example epoxides (e.g. epichlorhydrin).

The following Examples illustrate the invention; the temperatures are given in degrees Centigrade (° C).

EXAMPLE 1

α-Imidazol-1-yl-α-(p-chlorobenzyl)pinacolone (Compound 1)

Stage I : To sodium ethoxide solution [prepared by reacting sodium (6 g) with ethanol (200 ml] was added imidazole (17.3 g) in ethanol (50 ml) and the mixture was refluxed for one hour. The mixture was cooled and bromopinacolone (45 g) in ethanol (60 ml) was added; the mixture was refluxed for two hours and left at room temperature overnight with stirring. The solvent was removed in vacuo, water was added and the mixture extracted with methylene chloride. The organic layer was washed with water and dried (MgSO$_4$), and the solvent was removed. The residual oil was distilled to give α-imidazol-1-yl-pinacolone as a colourless oil, b.p. 138–142°/0.1 mm. The product contained unreacted imidazole, but was used for Stage II without further purification.

Stage Ii : To a suspension of sodium hydride [480 mg; 100%] in dimethyl formamide (5 ml) was added α-imidazol-1-yl-pinacolone (3.3 g) in dimethyl formamide (10 ml). After 3 hours, stirring at room temperature, p-chlorobenzyl chloride (3.2 g) in dimethylformamide (10 ml) was added and the mixture stirred at room temperature overnight. The dimethylformamide was removed in vacuo, and the residue was diluted with water and extracted with methylene chloride. The organic layer was washed with water, dried (Na$_2$SO$_4$) and the solvent was removed to give a yellow oil. This slowly solidified and was recrystallised from ether/petrol (40°–60°) to give, as colourless plates, α-imidazol-1-yl-α-(p-chlorobenzyl)-pinacolone, m.p. 98°–100°. Analysis; Calculated: C, 66.08; H, 6.59; N, 9.64%. Found: C, 66.49; H, 6.53; N, 9.58%.

EXAMPLE 2

α-Imidazol-1-yl-α-benzylpinacolone (Compound 2), m.p. 64°–66° (Analysis; Calculated. C, 74.04; H, 7.87; N, 11.51 %. Found: C, 73.82; H, 7.87; N, 11.83%) was prepared as described in Example 1 using benzyl chloride as the aralkylating agent.

EXAMPLE 3

α-Imidazol-1-yl-α-p-fluorobenzylpinacolone (Compound 3)

Stage I : α-Imidazol-1-ylpinacolone.

To sodium ethoxide solution [prepared by reacting sodium (6 g) with ethanol (200 ml)]was added imidazole (17.3 g) in ethanol (50 ml) and the mixture was refluxed for one hour. The mixture was cooled and bromopinacolone (45 g) in ethanol (60 ml) was added; the mixture was refluxed for two hours and left at room temperature overnight with stirring. The solvent was removed in vacuo, water was added and the mixture extracted with methylene chloride. The organic layer was washed with water and dried (MgSO$_4$), and the solvent was removed. The residual oil was distilled to give α-imidazol-1-yl-pinacolone as a colourless oil, b.p. 138°–142°/0.1 mm. The product contained unreacted imidazole, but was used for Stage II without further purification.

Stage II : To a suspension of sodium hydride [480 mg; 100%] in dimethylformamide (5ml) was added α-imidazol-1-ylpinacolone (3.3 g) in dimethylformamide (10 ml). After stirring for 3 hours at room temperature, p-fluorobenzylchloride (2.9 g) in dimethylformamide (10 ml) was added and the mixture was stirred at room temperature overnight. The dimethylformamide was removed in vacuo and the residue diluted with water and extracted with methylene chloride. The organic layer was washed with water, dried (Na$_2$SO$_4$) and the solvent was removed to give an orange oil. This was chromatographed over silica gel eluting with ethyl acetate. The product from the eluate was crystallised from petroleum ether (60°–80°) to give the title product as a white crystalline solid.

EXAMPLE 4

The compounds were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots. Vermiculite was used to cover the seed in the soil tests.

The test compounds were formulated either by bead-milling with aqueous Dispersol T or as a solution in acetone/ethanol which was diluted to the required concentration immediately before use. For the foliage diseases, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil and foliage one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period bethe progress of the reaction. The processes may also be carried out in the presence of a base, but preferably excess imidazole is present to remove liberated HX from the reaction. Other suitable bases are sodium hydride (although not when a hydroxylated solvent or diluent is used), alkali metal carbonates (such as potassium carbonate) and alkali metal hydroxides (such as potassium hydroxide). The reaction temperature depends upon the choice of reactants, solvent and base, but generally the reaction mixture is refluxed.

The processes generally involve dissolving the reactants in a solvent and, after allowing reaction to occur, isolating the product by removal of the reactant solvent in vacuo.

The unreacted imidazole is removed by extraction of the product with a suitable solvent and the extract is washed with water. A crystallisation or other purification procedure may then be carried out if desired.

The activated halo compounds may be made by any of the methods set out in the literature.

The compounds wherein Z is C = O may be converted in known manner to the C = O derivatives.

The compounds are active fungicides, particularly against the following diseases:

*Piricularia oryzae* on rice

*Puccinia recondita* and other rusts on wheat and rusts on other hosts

*Plasmopara viticola* on vines

*Erysiphe graminis* (powdery mildew) on barley and wheat and other powdery mildews on various hosts such as Sphaerotheca fulginea on cucumbers, Podosphaera leucotricha on apples and Uncinula necator on vines

*Botrytis cinerea* (grey mould) on tomatoes, strawberries, vines and other hosts Some of the compounds are active in the form of seed dressings against:

Fusarium spp., Septoria spp., Tilletia spp., and Pyrenophora spp. on cereals.

The compounds also have certain anti-bacterial and anti-viral activities.

They may be used as such for anti-fungal purposes but are more conveniently formulated into compositions for such usage.

The invention therefore also provides a fungicidal composition comprising, as an active ingredient, an imidazole compound or salt thereof, and a carrier for the active ingredient.

The invention also provides a method for combating pests, which are fungi, viruses or bacteria, which method comprises treating plants, seeds or trees with an imidazole compound or salt thereof as hereinbefore defined.

The compounds can be used to combat plant pests and treat plants or seeds in a number of ways, for example they can be applied, formulated or unformulated, directly to the foliage of a plant which is infected or likely to become infected, or they can be applied also to bushes and trees, to seeds or to other medium in which plants, bushes or trees are growing or are to be planted, or they can be sprayed on, dusted on or applied as a cream or paste formulation. Application can be to any part of the plant, bush or tree, for example to the foliage, stems, branches or roots, or to soil surrounding the roots.

The term "treating" as used herein refers to all these modes of application and the term "plant" includes seedlings, bushes and trees. Furthermore, the method of the invention includes preventative, protectant, prophylactic and eradicant treatment.

The compounds are preferably used for agricultural and horticultural purposes in the form of a composition. The type of composition used in any instance will depend upon the particular purpose envisaged.

The compositions may be in the form of dusting powders or granules comprising the active ingredient and a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed, for example, may comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersions or emulsions may be prepared by dissolving the active ingredient(s) in an organic solvent optionally containing wetting, dispersing or emulsifying agent(s) and then adding the mixture to water which may also contain wetting, dispersing or emulsifying agent(s). Suitable solvents are ethylene dichloride, isopropyl alcohol, propylene glycol, diacetone alcohol, toluene, kerosene, methylnaphthalene, the xylenes and trichloroethylene.

The compositions to be used as sprays may also be in the form of aerosols wherein the formulation is held in a container under pressure in the presence of a propellant, e.g. fluorotrichloromethane or dichlorodifluoromethane.

By including suitable additives, for example additives for improving the distribution, adhesive power and resistance to rain on treated surfaces, the different compositions can be better adapted for various utilities.

The compounds can be used as mixtures with fertilisers (e.g. nitrogen — or phosphorus — containing fertilisers). Compositions comprising only granules of fertiliser incorporating, for example coated with, the imidazole compound, are preferred. The invention therefore also provides a fertiliser composition comprising the imidazole compound.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonanionic agents.

Suitable cationic agents are quaternary ammonium compounds for example, cetyltrimethylammonium bromide. Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates). Suitable non-ionic agents are the condensation products of ethylene oxide with fatty alcohols such as oleyl alcohol or cetyl alcohol, or with alkyl phenols such as octylphenol, nonylphenol and octylcresol. Other non-ionic agents are the partial esters derived from long chain fatty acids and hexitol anhydrides, the condensation products of the said partial esters with ethylene oxide,

FUNGICIDALLY EFFECTIVE IMIDAZOLES AND USE THEREOF AGAINST FUNGAL PESTS

This invention relates to heterocyclic compounds which are imidazole compounds, to compositions containing them and to methods of combating pests (particularly fungal pests) using them.

The compounds have the general formula (I):

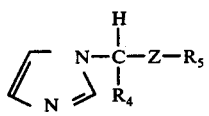

wherein $R_4$ is alkenyl, alkynyl or optionally substituted aralkyl (preferably benzyl), $R_5$ is cycloalkyl (e.g. cyclopentyl or cyclohexyl which can if desired be alkyl-substituted) or branched chain alkyl (particularly i-propyl or t-butyl), and Z is C = O or a derivative of said C = O; or a salt of such a compound.

The compounds can contain chiral centre(s). Normally the compounds are prepared in the form of racemic mixtures. However these and other mixtures can be separated into the individual isomers by methods known in the art.

The aralkyl group can be substituted by halogen (e.g. fluorine, chlorine, bromine or iodine), alkyl, nitro, trifluoromethyl, cyano, alkoxy or alkylenedioxy (e.g. methylenedioxy).

Examples of suitable alkyl, alkenyl, alkynyl or aralkyl groups are those having 1 to 8, preferably 1 to 7, carbon atoms, e.g. methyl, ethyl, propyl (n- or i-propyl), butyl (n-, i- or t-butyl), amyl (e.g. isopentyl), hexyl (e.g. 3,3-dimethylbutyl), heptyl, allyl, propynyl (e.g. propargyl), benzyl, 2-, 3- or 4-fluorobenzyl, 4-chlorobenzyl, 2-bromobenzyl-, 3,4-, 2,6- or 2,4-dichlorobenzyl, α-methylbenzyl, 4-cyanobenzyl, 2-, 3- or 4-nitrobenzyl, 3-methylbenzyl, α-methyl-4-chlorobenzyl, 3-trifluoromethylbenzyl, 3-nitro-4-chlorobenzyl, 2-methoxy-5-nitrobenzyl or 2-chloro-4,5-methylenedioxybenzyl.

Suitable C = O derivatives are ketals, hydrazones, semicarbazones, imines and oximes.

The salts of the compounds can be salts of organic or inorganic acids e.g. hydrochloric, sulphuric, acetic or oxalic acid.

Examples of suitable compounds wherein Z is C = O are shown in Table I.

TABLE I

| Compound No | $R_4$ | $R_5$ | Melting Point °C |
|---|---|---|---|
| 1 | CH₂—(C₆H₄)—Cl | t-Bu | 99–100° |
| 2 | CH₂Ph | t-Bu | 64–66° |
| 3 | CH₂—(C₆H₄)—F | t-Bu | 82–83° |
| 4 | CH₂—(C₆H₄)—CN | t-Bu | 121–124° |
| 5 | CH₂—(C₆H₄)—Br (ortho) | t-Bu | 100–102° |
| 6 | CH₂—(C₆H₃)—Cl,Cl | t-Bu | 97–98° |
| 7 | CH₂—(C₆H₄)—CF₃ | t-Bu | 69–71° |
| 8 | —CH(CH₃)—(C₆H₄)—Cl | t-Bu | 104–108° |
| 9 | CH₂—(C₆H₃)—Cl,Cl | t-Bu | 105–107° |

The compounds may be made by reacting imidazole or a salt thereof with the appropriate activated halo compound (for example an α-haloketone, α-haloacid, α-haloester, α-haloamide or substituted alkyl halide) using methods set out in the literature. Thus imidazole or a salt thereof, can be reacted with a compound of general formula (II):

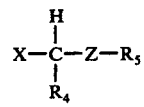

wherein X is halogen, preferably bromine or chlorine, and Z, $R_4$ and $R_5$ are as defined above.

Alternatively, the compounds wherein $R_4$ is other than hydrogen can be made by hydrocarbylating (e.g. with an appropriately substituted alkylating or aralkylating agent) a compound of general formula (III):

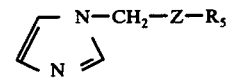

wherein $R_5$ and Z are as defined above, or a salt thereof, suitably in the presence of a base in a hydroxylic or non-hydroxylic solvent using methods set out in the literature.

These processes may in some cases be carried out by heating the reactants together in the absence of a solvent or diluent, but preferably a solvent is present. Suitable solvents are non-hydroxylic solvents such as acetonitrile (which is preferred), dimethylformamide, dimethyl sulphoxide, sulpholane and tetrahydrofuran. Hydroxylated solvents, for example methanol and ethanol, may be used in certain circumstances when the presence of the hydroxyl group does not interfere with